(12) United States Patent
Reed et al.

(10) Patent No.: US 11,925,549 B2
(45) Date of Patent: Mar. 12, 2024

(54) HEART VALVE WITH GATHERED SEALING REGION

(71) Applicant: Anteris Technologies Corporation, Eagan, MN (US)

(72) Inventors: Andrew Reed, Eagan, MN (US); Dave Mathieu, Eagan, MN (US); William Morris Leonard Neethling, Eagan, MN (US)

(73) Assignee: Anteris Technologies Corporation, Eagan, MN (US)

( * ) Notice: Subject to any disclaimer, the term of this patent is extended or adjusted under 35 U.S.C. 154(b) by 0 days.

(21) Appl. No.: 17/056,001

(22) PCT Filed: May 20, 2019

(86) PCT No.: PCT/US2019/033160
§ 371 (c)(1),
(2) Date: Nov. 17, 2020

(87) PCT Pub. No.: WO2019/222753
PCT Pub. Date: Nov. 21, 2019

(65) Prior Publication Data
US 2021/0212819 A1     Jul. 15, 2021

Related U.S. Application Data

(60) Provisional application No. 62/674,841, filed on May 22, 2018, provisional application No. 62/673,211, filed on May 18, 2018.

(51) Int. Cl.
*A61F 2/24*     (2006.01)

(52) U.S. Cl.
CPC .......... *A61F 2/2418* (2013.01); *A61F 2/2436* (2013.01); *A61F 2250/0069* (2013.01)

(58) Field of Classification Search
CPC .................. A61F 2/2418; A61F 2/2436; A61F 2250/0069
See application file for complete search history.

(56) References Cited

U.S. PATENT DOCUMENTS

| 4,624,822 A | 11/1986 | Arru et al. |
| 6,491,511 B1 | 12/2002 | Duran et al. |

(Continued)

FOREIGN PATENT DOCUMENTS

| CN | 203736349 | 7/2014 |
| EP | 2777618 A1 | 9/2014 |

(Continued)

OTHER PUBLICATIONS

Knee Hiang Lim et al., Flat or Curved Pericardial Aortic Valve Cusps: A Finite Element Study, Journal of Heart Valve, vol. 13, No. 5 (Sep. 2004).

(Continued)

*Primary Examiner* — Suba Ganesan
(74) *Attorney, Agent, or Firm* — Fish & Richardson P.C.

(57) ABSTRACT

A valve for endovascular heart valve repair that provides improved sealing of the valve against the native wall. The valve assembly has a sealing region at a distal end of the valve. The sealing region having a delivery position and a sealing position, wherein in the delivery position, the sealing region has a first length, and in the sealing position, the sealing region has a second length less than the first length and a thickness in the sealing position is greater in the sealing position than in the delivery position.

9 Claims, 3 Drawing Sheets

(56) References Cited

U.S. PATENT DOCUMENTS

| | | | |
|---|---|---|---|
| 6,682,559 B2 | 1/2004 | Myers et al. | |
| 7,025,780 B2 | 4/2006 | Gabbay | |
| 7,087,079 B2 | 8/2006 | Navia et al. | |
| 8,778,018 B2 | 7/2014 | Iobbi | |
| 8,992,599 B2 | 3/2015 | Thubrikar et al. | |
| 9,011,525 B2 | 4/2015 | Claiborne, III et al. | |
| 9,095,430 B2 | 8/2015 | Cunanan et al. | |
| 9,192,470 B2 | 11/2015 | Cai et al. | |
| 9,205,172 B2 | 12/2015 | Neethling et al. | |
| 9,259,313 B2 | 2/2016 | Wheatley | |
| 9,301,835 B2 | 4/2016 | Campbell et al. | |
| 9,554,902 B2 | 1/2017 | Braido et al. | |
| 9,744,037 B2 | 8/2017 | Kheradvar et al. | |
| 9,763,780 B2 | 9/2017 | Morriss et al. | |
| 11,135,059 B2 | 10/2021 | Hammer et al. | |
| 11,464,635 B2 | 10/2022 | Reimer et al. | |
| 2003/0069635 A1 | 4/2003 | Cartledge et al. | |
| 2005/0123582 A1 | 6/2005 | Sung et al. | |
| 2005/0137687 A1 | 6/2005 | Salahieh et al. | |
| 2005/0203614 A1 | 9/2005 | Forster et al. | |
| 2005/0240262 A1 | 10/2005 | White | |
| 2006/0020327 A1 | 1/2006 | Lashinski et al. | |
| 2008/0288055 A1 | 11/2008 | Paul, Jr. | |
| 2010/0049313 A1 | 2/2010 | Alon et al. | |
| 2011/0066224 A1 | 3/2011 | White | |
| 2011/0238167 A1 | 9/2011 | Dove et al. | |
| 2012/0277855 A1 | 11/2012 | Lashinski et al. | |
| 2013/0018458 A1 | 1/2013 | Yohanan et al. | |
| 2013/0184811 A1 | 7/2013 | Rowe et al. | |
| 2013/0204360 A1 | 8/2013 | Gainor | |
| 2013/0310927 A1 | 11/2013 | Quintessenza | |
| 2014/0005772 A1 | 1/2014 | Edelman et al. | |
| 2014/0031924 A1 | 1/2014 | Bruchman et al. | |
| 2014/0107772 A1* | 4/2014 | Li | A61F 2/2418 623/2.17 |
| 2014/0180393 A1* | 6/2014 | Roeder | A61F 2/06 623/1.15 |
| 2014/0277417 A1 | 9/2014 | Schraut et al. | |
| 2014/0324160 A1 | 10/2014 | Benichou et al. | |
| 2015/0134056 A1 | 5/2015 | Claiborne, III et al. | |
| 2015/0142104 A1 | 5/2015 | Braido | |
| 2015/0209141 A1 | 7/2015 | Braido et al. | |
| 2015/0216663 A1 | 8/2015 | Braido et al. | |
| 2015/0320556 A1 | 11/2015 | Levi et al. | |
| 2016/0128831 A1 | 5/2016 | Zhou et al. | |
| 2016/0135951 A1 | 5/2016 | Salahieh et al. | |
| 2016/0143732 A1 | 5/2016 | Glimsdale | |
| 2016/0158007 A1 | 6/2016 | Centola et al. | |
| 2016/0175095 A1 | 6/2016 | Dienno et al. | |
| 2016/0220365 A1 | 8/2016 | Backus et al. | |
| 2016/0317293 A1 | 11/2016 | Matheny et al. | |
| 2016/0331532 A1 | 11/2016 | Quadri | |
| 2016/0367360 A1 | 12/2016 | Cartledge et al. | |
| 2016/0367364 A1 | 12/2016 | Torrianni et al. | |
| 2017/0049566 A1 | 2/2017 | Zeng et al. | |
| 2017/0056170 A1 | 3/2017 | Zhu et al. | |
| 2017/0119525 A1 | 5/2017 | Rowe et al. | |
| 2017/0189174 A1* | 7/2017 | Braido | A61F 2/2436 |
| 2017/0312075 A1 | 11/2017 | Fahim et al. | |
| 2018/0028312 A1 | 2/2018 | Thill et al. | |
| 2018/0228603 A1 | 8/2018 | Racchini et al. | |
| 2019/0117390 A1 | 4/2019 | Neethling et al. | |
| 2021/0212819 A1 | 7/2021 | Reed et al. | |
| 2021/0212822 A1 | 7/2021 | Reed et al. | |
| 2021/0212823 A1 | 7/2021 | Reed et al. | |

FOREIGN PATENT DOCUMENTS

| | | |
|---|---|---|
| EP | 3697343 | 8/2020 |
| JP | 2008-264553 | 11/2008 |
| JP | 2015519187 A | 7/2015 |
| WO | 2001076510 A2 | 10/2001 |
| WO | 2003/030776 | 4/2003 |
| WO | 2007013999 A2 | 2/2007 |
| WO | 2011072084 A2 | 6/2011 |
| WO | 2011109450 A2 | 9/2011 |
| WO | 2014204807 A1 | 12/2014 |
| WO | 2015126712 A1 | 8/2015 |
| WO | 2015173794 A1 | 11/2015 |
| WO | 2017031155 A1 | 2/2017 |

OTHER PUBLICATIONS

Search Report and Written Opinion for related PCT Application No. PCT/US2019/033160 dated Sep. 3, 2019. (9 pages).

* cited by examiner

HEART VALVE WITH GATHERED SEALING REGION

CROSS-REFERENCE TO RELATED APPLICATIONS

The present disclosure claims priority to U.S. Provisional Application No. 62/673,211, filed May 18, 2018, and to U.S. Provisional Application No. 62/674,841, filed May 22, 2018, entitled "Heart Valve With Gathered Sealing Region", the contents of which are hereby incorporated by reference herein in their entirety.

FIELD OF THE INVENTION

The present disclosure relates to novel and advantageous devices and methods for a transcatheter valve replacement devices.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Native heart valves may need to be replaced when a patient has a condition such as congenital heart defect or valvular heart disease. A diseased heart valve may result in regurgitation, where the valve is not properly function and blood flows in a direction opposite the normal direction of the flow, and/or stenosis, where the valve has narrowed through in some instances calcification of the valve, some obstruction of the valve such as plaque, or inflammation. Heart valves may be replaced through surgical repair or a valve deployed relative to the native heart valve through a transcatheter approach. Transcatheter valve replacement devices generally comprise leaflets of tissue that are attached to an expandable or self-expanding stent construct that is crimped onto a catheter for deployment. The stent is advanced to the location of the troubled heart valve, where it expands or is expanded by a balloon or other means. Once seated in the valve, blood flow and the muscles of the heart will result in the tissue leaflets to open and close.

One challenge affecting transcatheter valve replacement devices is the French size of the catheter required to deliver the valve replacement device to the affected native heart valve through the vasculature. There is a desire to reduce the French size of the catheter to improve maneuverability of the catheter as it is advanced to the site of the affected native heart valve.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

A heart valve of the present disclosure has a sealing region that extends distally from the distal end of the stent to which the heart valve is connected. The sealing region is elongated in the delivery position, but can be gathered from its elongated state into a crimped state while in the sealing position. In some embodiments, the sealing region in the sealing position may overlap a distal portion of the stent. The sealing region in the sealing region is thicker than in the delivery position and has a plurality of sealing features on the outer surface of the sealing region. The sealing features abut the native valve wall to assist with sealing of the valve and may encourage cellular growth (with or without a coating) to enable better sealing of the valve.

In at least one embodiment of the present disclosure, a system for endovascular heart valve repair comprises a delivery catheter comprising a retractable sheath and a valve assembly disposed within the retractable sheath in a delivery position. The valve assembly comprises a stent and a sealable heart valve connected to the stent. The stent has an outer surface and an inner surface defining a stent lumen. The sealable heart valve has a proximal end and a distal end. The sealable heart valve has outer surface, an inner surface defining a valve lumen, and a thickness between the outer surface and the inner surface. The sealable heart valve may have a sealing region that extends distally from the distal end of the stent. The sealing region may have a delivery position and a sealing position. In the delivery position, the sealing region may have a first length, and in the sealing position, the sealing region may have a second length less than the first length and a thickness in the sealing position is greater in the sealing position than in the delivery position. The system may comprise at least one gathering wire connected at a distal end near the distal end of the sealable heart valve in the delivery position. The sealable heart valve may comprise at least one gathering wire connector for engaging the sealable heart valve with the at least one gathering wire. The at least one gathering wire may be pulled proximally until the sealing region is in the sealing position. In some embodiments, the at least one gathering wire may then be released from the sealable heart valve when the sealing region is in the sealing position. In some embodiments, the sealing region may comprise a plurality of ridges. In at least some embodiments, the sealing region comprises a valley between a first ridge and a second ridge in the delivery position. In the sealing position, the first ridge may abut the second ridge. In some embodiments, the sealable heart valve comprises a biomaterial, which may be a cross-linked biomaterial. In at least one embodiment, the sealable heart valve comprises a leaflet region between the proximal end and the sealing region, wherein the leaflet region comprises at least one leaflet and at least one commissure.

In some embodiments of the disclosure, a sealable heart valve comprises an outer surface extending from a proximal end to a distal end; an inner surface extending from the proximal end to the distal end, wherein the inner surface defines a lumen; and a thickness between the outer surface and the inner surface. The sealable heart valve comprises a leaflet region between the proximal end and the distal end. The leaflet region may comprise at least one leaflet and at least one commissure. In some embodiments, the sealable heart valve comprises a sealing region extending proximally from the distal end to the leaflet region. The sealing region has a delivery position and a sealing position. In the delivery position, the sealing region has a first length, and in the sealing position, the sealing region has a second length less than the first length. In some embodiments, the sealing region comprises a plurality of ridges. The sealing region may comprise a valley between a first ridge and a second ridge in the delivery position. In the sealing position, the first ridge may abut the second ridge. The ridges may be formed into the material of the sealing region using a mandrel or other three dimensional forming process. In other embodiments, the ridges may be formed by varying the thickness of the material along the sealing region, where the ridges are areas of greater thickness than the valleys. In still other embodiments, other techniques may be used to form the ridges and valleys either alone or in combination with these methods. For example, the sealing region may have a stitched pattern or thinned in certain areas to allow for a desired sealing position. In some embodiments, the sealable heart valve may comprise at least one gathering wire connector for communication with a gathering wire used to pull the sealing region into the sealing position.

In some embodiments of the disclosure, a valve assembly for endovascular heart valve repair comprises a stent and a sealable heart valve connected to the stent. The stent has a proximal end and a distal end, the stent having an outer surface, an inner surface defining a stent lumen. The sealable heart has a proximal end and a distal end. The sealable heart valve has an outer surface, an inner surface that defines a valve lumen, and a thickness between the outer surface and the inner surface. The sealable heart valve has a sealing region that extends distally from the distal end of the stent. The sealing region has a delivery position and a sealing position. In the delivery position, the sealing region has a first length, and in the sealing position, the sealing region has a second length less than the first length and a thickness in the sealing position is greater in the sealing position than in the delivery position. The valve assembly may comprise at least a first ridge and a second ridge with a valley between the first ridge and the second ridge. In the sealing position, the first ridge abuts the second ridge. In some embodiments, the sealable heart valve comprises at least one gathering wire connector.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure relates to replacement heart valves for use in the mitral valve, tricuspid valve, aortic valve or pulmonary valve of the heart. In some circumstances, a replacement heart valve may be disposed within the native valve such that portions of the replacement heart valve, or portions of a device such as a stent attached to the replacement heart valve, are adjacent to the native heart valve.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Figure 1:
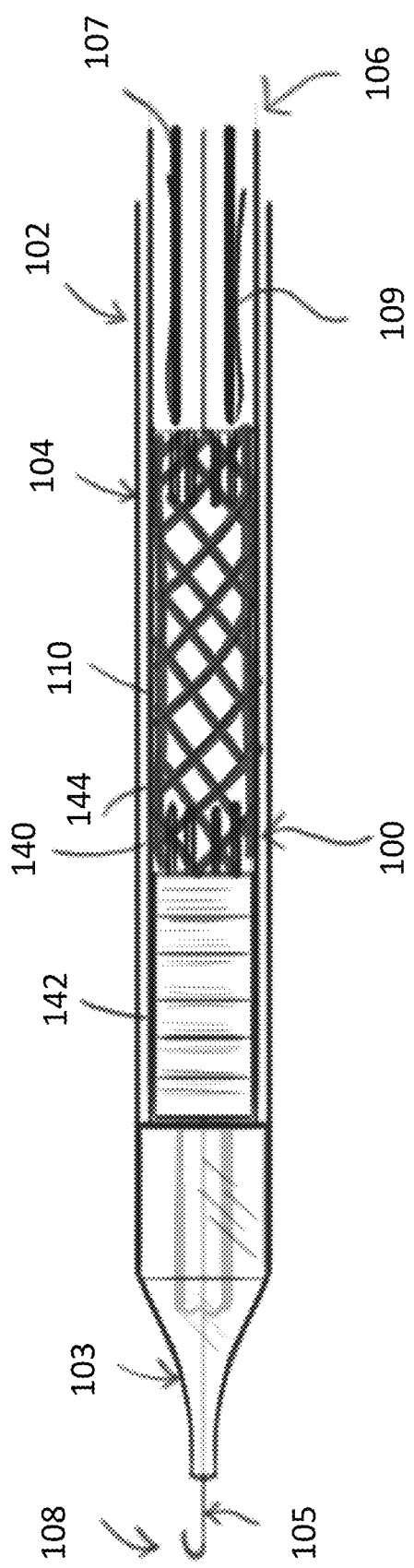
FIG. 1 is a side view of a replacement heart valve assembly disposed within the retractable sheath of a catheter in a delivery position.
Figure 2:
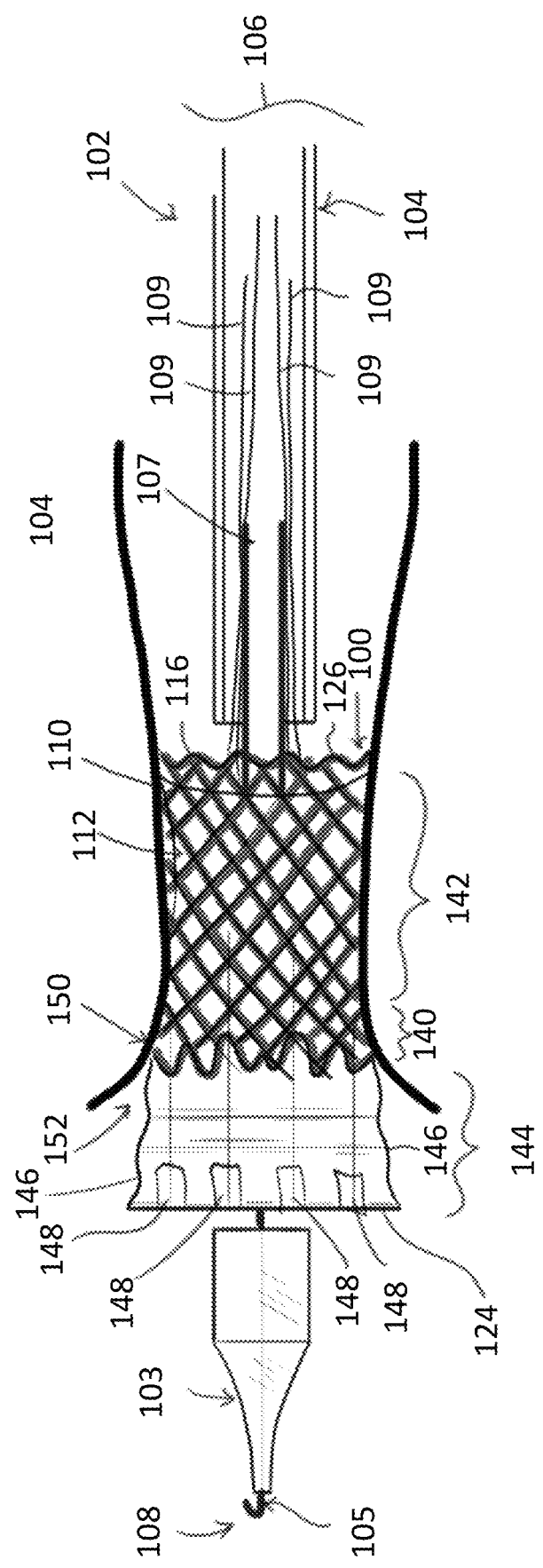
FIG. 2 is a side view of the replacement heart valve assembly of FIG. 1 in the deployed position.
Figure 3:
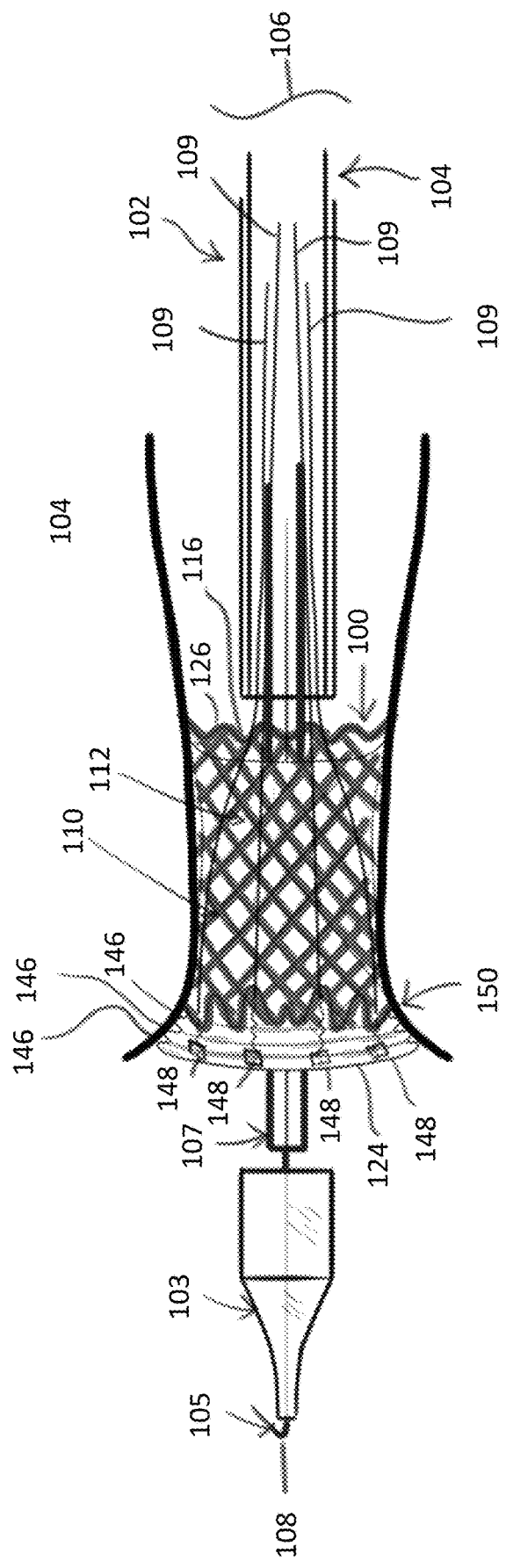
FIG. 3 is a side view of the replacement heart valve assembly of FIG. 1 in the sealing position.

FIGS. 1-3 show an embodiment of the valve of the present disclosure. FIG. 1 shows the valve assembly 100 loaded within a catheter assembly 102, the catheter assembly 102 having a retractable sheath 104 with a proximal end 106 and a distal end 108. Although this application uses the terms "proximal" and "distal" in the same relative manner with respect to the devices shown in the figures, it is within the scope of this invention that "proximal" and "distal" can be interchanged with "distal" and "proximal" in other embodiments. The catheter assembly 102 may further comprise a tip 103 near the distal end 108, a guidewire 105, and a guidewire shaft 107 coaxial with the retractable sheath 104. The catheter assembly 102 may comprise at least one gathering wire 109 connected to the valve assembly 100 for pulling a portion of the valve assembly 100 in an axial direction to help form a seal against the native wall. The at least one gathering wire 109 may be positioned between the guidewire shaft 107 and the retractable sheath. As shown in FIG. 1, the catheter assembly 102 has four gathering wires 109, although it is contemplated by this disclosure that any number of gathering wires 109 may be suitable to control the sealing of the valve assembly 100 against the native wall. The valve assembly 100 is disposed within the retractable sheath 104 in a delivery position. The valve assembly 100 comprises a stent 110 and a valve 112 partially disposed within the stent 110.

The stent 110 may be a balloon expandable, self-expanding, or otherwise expandable stent capable of expanding from a delivery position to a deployed position. The stent 110 has a distal end 114, a proximal end 116, an outer surface 118 extending between the distal end 114 and the proximal end 116, and an inner surface 120 extending between the distal end 114 and the proximal end 116 and defining a stent lumen 122 therein.

The valve 112 may comprise a tissue material. The valve 112 may be constructed, in some embodiments, from a single piece of tissue material. In other embodiments, the valve 112 may be constructed from multiple pieces of tissue material. In some embodiments, the tissue material may be a biomaterial. In some embodiments, the tissue material may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings. In some embodiments, the artificial tissue may be combined with fabrics or other coatings to encourage cellular growth. The valve 112 may be constructed out of any of these materials, either alone or in combination. The valve 112 may have coatings, fabric, or other materials embedded in a sealing region of the valve to facilitate desired sealing of the valve 112.

The valve 112 has a distal end 124, a proximal end 126, an outer surface 128 extending between the distal end 124 and the proximal end 126, and an inner surface 130 extending between the distal end 124 and the proximal end 126 and defining a valve lumen 132 therein. The valve 112 is partially disposed within the stent lumen 122 such that a portion of the valve's outer surface 128 abuts the stent's inner surface 120. The valve 112 may be connected to the stent 110 by sutures, staples, adhesive, or any other means of connecting the stent 110 to the valve 112. In some embodiments, not shown, a layer of a material may overlap at least a portion of the outer surface 118 of the stent to assist, at least in part, with connecting the valve to the stent. The layer of material may comprise tissue material or a suitable polymer such as, but not limited to, PTFE.

In some embodiments, the valve 112 comprises a leaflet region 140 and a sealing region 144 extending distally from the leaflet region 140 to the distal end 124 of the valve. The valve may further comprise a support region 142 extending proximally from the leaflet region 140 to the proximal end 126 of the valve 112. The leaflet region 140 comprises at least one valve leaflet (not shown) and at least one valve commissure (not shown). In some embodiments, the leaflet region 140 may have at least three valve leaflets and at least three valve commissures. The valve 112 may, in some embodiments, be attached to the stent 110 at the leaflet region 140. In at least one embodiment, the valve 112 may be attached to the stent 110 at each of the valve commissures. The support region 142 may extend proximally from the leaflet region towards the proximal end 116 of the stent 110 and abuts at least a portion of the stent 110. In some embodiments, the proximal end 126 of the valve 112 may be distal to the proximal end 116 of the stent 110. The sealing region 144 extends distally from the distal end 114 of the stent 110 to the distal end 124 of the valve 112. In some embodiments, the sealing region 144 may have a thickness over at least a portion of the sealing region that is less than the thickness of the support region. FIG. 1 shows the sealing region 144 extending generally flat within the sheath 104, however in other embodiments the sealing region 144 may not be generally flat in some embodiments in this loaded position. Having the sealing region 144 extending distally from the distal end of the stent 110 allows the valve assembly, when in the loaded position, to have a reduced circumferential profile and therefore the valve assembly can be loaded into smaller sized catheters.

The sealing region 144 may comprise a plurality of sealing features 146 on the outer surface 128. In at least one embodiment, the sealing features 146 may include a plurality of axially adjacent annular rings of varying thickness forming ridges and valleys along the sealing region 144. The ridges may have a thickness that is greater than a thickness of the valleys. In some embodiments, the sealing region may be formed, for example on a mandrel, to have a plurality of peaks and valleys, which may have equal thickness. The sealing region 144 may further comprise a coating on at least a portion of the outer surface 128 to improve sealing of the valve against the native valve.

The sealing region 144 may further comprise at least one gathering wire connector 148 for releasably connecting to the gathering wire 109. The at least one gathering wire connector 148 may be disposed on the inner surface 130 or on the outer surface 128 at the sealing region 144. The at least one gathering wire connector 148 may include a radiopaque marker or other imaging technology to assist with positioning of the valve and/or confirming sealing against the native wall.

FIG. 2 shows the valve assembly 100 in a deployed position with the retractable sheath 104 retracted proximally from the valve assembly 100. The valve assembly 100 is positioned within the native valve with the stent 110 and valve 112 expanded against the native wall 150. As shown in FIG. 2, a gap 152 is often present between the valve assembly 100 and the native wall 150. Once in the deployed position, the gathering wires 109 may be pulled in a proximal direction towards stent 110, thus shortening the axial length of the sealing region 144 while increasing the thickness of the sealing region 144 to seal the valve assembly 100 against the native wall 150 to minimize, if not fully close, the gap 152 in the sealing position as shown in FIG. 3. After the sealing region 144 is in the sealing position, each of the gathering wires 109 may be released from the gathering wire connectors 148. In at least one embodiment, the gathering wire connectors 148 may include a feature that at least partially cuts the gathering wires within the connector when the sealing region 144 is fully in the sealing position to release the gathering wires. In some embodiments, at least a portion of the gathering wire 109 may remain connected to the gathering wire connectors 148 while the sealing region 144 is in the sealing position to keep a desired tension on the sealing region for at least a period of time after the catheter assembly is fully withdrawn from the vasculature. The gathering wire 109 may comprise a dissolvable material such as polydioxanone, polyglycolic acid, polyglyconate, polylactic acid, polydioxanone, collagen, or other artificial tissue.

In the sealing position, shown in FIG. 3, at least one of the surface features 146, such as a ridge, abuts an axially adjacent surface feature 146, such as a second ridge. In at least one embodiment the surface features 146 form an irregularly contoured surface. The outer surface 128 of the sealing region 144 appears to be ribbed. The outer surface 128 may be at least partially coated with a material that encourages cellular growth to improve the sealing of the sealing region 144 against the native wall 150. In some embodiments, when the sealing region 144 is in the sealing position, a portion of the sealing region 144 overlaps the distal end 114 of the stent 110. In at least one embodiment, in the sealing position, the sealing region may have a diameter greater than the stent 110.

The ridges may be formed into the material of the sealing region using a mandrel or other three dimensional forming process. In other embodiments, the ridges may be formed by varying the thickness of the material along the sealing region, where the ridges are areas of greater thickness than the valleys. In still other embodiments, other techniques may be used to form the ridges and valleys either alone or in combination with these methods. For example, the sealing region may have a stitched pattern or thinned in certain areas to allow for a desired sealing position.

Although the above disclosure describes a valve assembly comprising both the valve and a stent, it is contemplated by this disclosure that embodiments of this invention may include a valve that is not attached to a stent.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the devices described herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A system for endovascular heart valve repair, the system comprising:
    a delivery catheter comprising a retractable sheath; and
    a valve assembly that is positionable within the retractable sheath in a delivery position, the valve assembly comprising:
        a stent having a proximal end and a distal end, the stent having an outer surface and an inner surface defining a stent lumen; and
        a sealable heart valve connected to the stent, the sealable heart valve having a proximal end and a distal end, the sealable heart valve having an outer surface, an inner surface defining a valve lumen, and a thickness between the outer surface and the inner surface, wherein the sealable heart valve comprises:
            a leaflet region comprising at least one leaflet and at least one commissure, wherein the leaflet region is disposed within the stent lumen;
            a support region extending proximally from the leaflet region within the stent lumen to the proximal end of the sealable heart valve; and
            a sealing region comprising at least one gathering wire connector, the sealing region extending distally from the leaflet region to the distal end of the sealable heart valve, the sealing region having: (i) a delivery position and (ii) a sealing position in which the sealing region is gathered to form a plurality of ridges,
    wherein the sealing region has a first length when in the delivery position and a second length that is less than the first length when in the sealing position,
    wherein the sealing region has a first thickness when in the delivery position and a second thickness that is greater than the first thickness when in the sealing position,
    wherein the sealing region flares radially outward when in the sealing position, and
    wherein the sealing region has a larger outer diameter when in the sealing position than a largest outer diameter of the stent.

2. The system of claim 1, further comprising at least one gathering wire having a distal end connected to at least one gathering connector near the distal end of the sealable heart valve in the delivery position.

3. The system of claim 2, wherein the at least one gathering wire is configured to be pulled proximally to transition the sealing region from the delivery position to the sealing position.

4. The system of claim 3, wherein the at least one gathering wire is released from the sealable heart valve when the sealing region is fixedly in the sealing position.

5. The system of claim 1, wherein the sealing region comprises a valley between a first ridge and a second adjacent ridge in the delivery position.

6. The system of claim 5, wherein in the sealing position, the first ridge abuts the second adjacent ridge.

7. The system of claim 1, wherein the leaflet region and the sealing region are formed from a single piece of tissue material.

8. A valve assembly for endovascular heart valve repair, the valve assembly comprising:

a stent having a proximal end and a distal end, the stent having an outer surface, an inner surface defining a stent lumen; and a sealable heart valve connected to the stent, the sealable heart valve having a proximal end and a distal end, the sealable heart valve having an outer surface, an inner surface defining a valve lumen, and a thickness between the outer surface and the inner surface, wherein the sealable heart valve comprises:

- a leaflet region comprising at least one leaflet and at least one commissure, wherein the leaflet region is disposed within the stent lumen;
- a support region extending proximally from the leaflet region within the stent lumen to the proximal end of the sealable heart valve; and
- a sealing region comprising at least one gathering wire connector, the sealing region extending distally from the leaflet region to the distal end of the sealable heart valve, the sealing region having: (i) a delivery position and (ii) a sealing position in which the sealing region is gathered to form a plurality of ridges, wherein the sealing region has a first length when in the delivery position and a second length that is less than the first length when in the sealing position, wherein the sealing region has a first thickness when in the delivery position and a second thickness that is greater than the first thickness when in the sealing position, wherein the sealing region flares radially outward when in the sealing position, and wherein the sealing region has a larger outer diameter when in the sealing position than a largest outer diameter of the stent.

9. The valve assembly of claim 8, wherein the leaflet region and the sealing region are formed from a single piece of tissue material.

* * * * *